(12) United States Patent
Ghose et al.

(10) Patent No.: US 11,707,208 B2
(45) Date of Patent: Jul. 25, 2023

(54) METHOD AND SYSTEM FOR TREMOR ASSESSMENT USING PHOTOPLETHYSMOGRAPHY (PPG)

(71) Applicant: Tata Consultancy Services Limited, Mumbai (IN)

(72) Inventors: Avik Ghose, Kolkata (IN); Nasimuddin Ahmed, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 184 days.

(21) Appl. No.: 17/200,973

(22) Filed: Mar. 15, 2021

(65) Prior Publication Data

US 2021/0298641 A1    Sep. 30, 2021

(30) Foreign Application Priority Data

Mar. 24, 2020  (IN) .............................. 202021012897

(51) Int. Cl.
  *A61B 5/11* (2006.01)
  *A61B 5/00* (2006.01)
(52) U.S. Cl.
  CPC .......... *A61B 5/1101* (2013.01); *A61B 5/1126* (2013.01); *A61B 5/7257* (2013.01)
(58) Field of Classification Search
  CPC .... A61B 5/1101; A61B 5/4082; A61B 5/7235
  (Continued)

(56) References Cited

U.S. PATENT DOCUMENTS

| 2013/0018283 A1* | 1/2013 | Halkias | ................ | A61B 5/1101 600/595 |
| 2016/0007934 A1* | 1/2016 | Arnold | ................ | A61B 5/4809 600/595 |

(Continued)

FOREIGN PATENT DOCUMENTS

| AT | 515976 A1 * | 1/2016 | ......... A61B 5/02416 |
| EP | 3501381 A1 * | 6/2019 | ......... A61B 5/02416 |
| EP | 3501382 A1 * | 6/2019 | ......... A61B 5/02416 |

OTHER PUBLICATIONS

Madhav, K. V., Krishna, E. H., & Reddy, K. A. (2016). Extraction of surrogate respiratory activity from pulse oximeter signals using SSA. 2016 International Conference on Electrical, Electronics and Optimization Techniques (ICEEOT): 1717-21;521. IEEE. (Year: 2016).*

(Continued)

*Primary Examiner* — Daniel L Cerioni
*Assistant Examiner* — Jonathan E. Cooper
(74) *Attorney, Agent, or Firm* — Finnegan, Henderson, Farabow, Garrett & Dunner, LLP

(57) ABSTRACT

Existing wearable device-based approaches to capture a_tremor signal have accuracy limitations due to usage of accelerometer sensor with inherent noisy nature. The method and system disclosed herein taps characteristics of the PPG sensor of being sensitive to the motion artifact, as an advantage, to capture tremor_signals present in the PPG sensor. The method disclosed herein describes an approach to extract tremor_signals of interest from the PPG signal by performing a Singular Spectrum Analysis (SSA) followed by spectrum density estimation. The SSA comprises performing embedding on the acquired PPG signal, performing Principal Component Analysis (PCA) on the embedded signal and reconstructing the rest tremor signal from the significant principal components identified post the PCA.

(Continued)

Further, the spectrum density estimation detects a dominant frequency present in the principal components, which is the dominant frequency associated with the rest tremor.

13 Claims, 5 Drawing Sheets

(58) Field of Classification Search
USPC .......................................................... 600/595
See application file for complete search history.

(56) References Cited

U.S. PATENT DOCUMENTS

| | | | |
|---|---|---|---|
| 2016/0220151 A1* | 8/2016 | Zizi | A61B 5/7235 |
| 2016/0361021 A1* | 12/2016 | Salehizadeh | A61B 5/02416 |
| 2016/0367198 A1 | 12/2016 | Chon et al. | |
| 2017/0215808 A1 | 8/2017 | Shimol et al. | |
| 2018/0247713 A1 | 8/2018 | Rothman | |
| 2019/0365286 A1 | 12/2019 | Powers, III et al. | |

OTHER PUBLICATIONS

Decision to Grant a European Patent Pursuant to Article 97(1) EPC dated Jun. 30, 2022, for EP Patent Application No. 21 162 394.7; 2 pages.

Communication about intention to grant a European Patent received from the European Patent Office in EP Application No. 21 162 394.7, 6 pages, dated Feb. 7, 2022.

Extended European Search Report issued by the European Patent Office in counterpart European Patent Application No. 21 162 394.7, 5 pages, dated Aug. 9, 2021.

Eftaxias et al.; "Detection of Parkinson's Tremor from EMG Signals; A Singular Spectrum Analysis Approach", IEEE International Conference on Digital Signal Processing (DSP), IEEE, pp. 398-402, (2015).

Pereira et al.; "A survey on computer-assisted Parkinson's Disease diagnosis", Artificial Intelligence in Medicine, Elsevier, NL, vol. 95, pp. 48-63, (2018).

Adhikari et al.; "Real-time physiological tremor estimation using recursive singular spectrum analysis", 2017 39th Annual International Conference of the IEEE Engineering in Medicine and Biology Society (EMBC), IEEE, pp. 3202-3205, (2017).

Ahmed et al: "Heart Rate Estimation Algorithm From Wrist-based Photoplethysmogram Using Subspace Learning Method", 2019 IEEE International Conference on Pervasive Computing and Communications Workshops (PERCOM Workshops), IEEE, pp. 145-150, (2019).

Pham et al., "Nonlinear Dynamics Analysis of Short-Time Photoplethysmogram in Parkinson's Disease," IEEE International Conference on Fuzzy Systems (FUZZ) (2018).

\* cited by examiner

METHOD AND SYSTEM FOR TREMOR ASSESSMENT USING PHOTOPLETHYSMOGRAPHY (PPG)

PRIORITY CLAIM

This U.S. patent application claims priority under 35 U.S.C. § 119 to: India Application No. 202021012897, filed on 24 Mar. 2020. The entire contents of the aforementioned application are incorporated herein by reference.

TECHNICAL FIELD

The embodiments herein generally relate to the field of health monitoring and analysis using sensor data acquired from wearable sensors and, more particularly, to a method and system for tremor assessment using Photoplethysmography (PPG).

BACKGROUND

Wearable device-based health monitoring enables non-clinal measurement of health parameters, thus providing non-invasive sensing with seamless monitoring of health parameters. Such seamless monitoring of health parameters of a subject enables to tap early symptoms and predict onset of a particular disease. Most of the current work on health monitoring using wearable technology focusses on detecting parameters such as heart rate, breath rate, monitoring motion of a subject for Activities of Daily Living (ADL) and so on.

Diseases such as Parkinson's Disease (PD) is a progressive neurodegenerative condition that manifests motor and non-motor dysfunction. The symptoms associated with PD are characterized by TRAP—Tremor, Rigidity (muscular stiffness), Akinesia (a movement disorder) and Postural instability. Tremor especially the Rest Tremor is the most cardinal symptom occurs in earlier stages of Parkinson. It is defined as an involuntarily rhythmic movement persists on various part of the body (usually a hand or the fingers) at rest. Especially, in Rest Tremors the fingers are majorly affected and poses a symptom called Pill Rolling. Despite the numerous researches, the cure for Parkinson is not attained yet. The treatment procedure relies on the medications which yield only symptomatic relief. As the disease progresses, the effect of medications gradually diminishes and the severity of symptoms augment. According to the severity of the symptom, the dose of the medications needs to be altered.

Conventional methods to assess the TRAP symptoms require clinical tests/tasks under observation of an expert. Limitations of such clinical tests is that the results are highly subjective are dependent on observations and experience of the expert, further regular visits add to cost and are inconvenient. Another approach followed may be self-reporting by the subject, which in majority of cases is erroneous due to lack of expert observation.

With the advent of wearable technologies, research works have proposed detection and assessment of Rest Tremor using wearable sensors. These existing approaches have used EMG sensors for detecting the tremor. The major limitation for EMG modality is that it is not ubiquitous. Moreover, the commercially available wearable devices such as Smartwatches or Fitness devices usually are not equipped with the EMG sensors. Recently, Inertial Measurement Unit (IMU) (accelerometer and gyroscope) sensors have gained popularity in the assessment of tremor owing to its compact size and prevalence in Wearable system. Several existing works employed customized Wrist-watch-type wearable devices and explored various machine learning or deep learning-based algorithms for automatic assessment of Parkinsonian tremor. Since, the hand finger is greatly affected by the Rest Tremor, the existing approaches deployed the accelerometer sensor on finger. However, the placement of the sensor on the finger or cumbersome Glove form factor can cause inconvenience to the patient.

Since, the intensity of the tremor at finger dies down on the wrist, sensing the finger tremor from the wrist is quite a stringent problem. Although the wrist-based accelerometer approaches are attractive, the sensor is inherently noisy in nature. Even when it is put rest condition, the sensor bias exists, and the strength of the bias is significant. In specific cases, when the finger would possess a low intensity vibration, the tremor could be buried in bias noises. Particularly, in Pill Rolling symptoms this situation would be imperative. Another potential problem is the gravitational force which causes a gravitational component in the acceleration signal and it needs to be discarded to assess the tremor signal.

Further, while exploring other sensor modalities in detecting tremors, hardly any attempts have been observed towards utilizing Photoplethysmography (PPG) for assessment of tremor signals. An existing literature mentions potential use of short-time PPG signals for differentiating patients with Parkinson's disease (PD) from healthy control (HC) subjects with nonlinear dynamics analysis. However, the focus of the existing work is limited to classification of subjects into PD and HC based on feature extraction from the acquired PPG signal. The existing work does not provide tremor signal assessment associated with the PD.

SUMMARY

Embodiments of the present disclosure present technological improvements as solutions to one or more of the above-mentioned technical problems recognized by the inventors in conventional systems.

For example, in one embodiment, a method for tremor assessment using Photoplethysmography (PPG) is provided.

The method comprises receiving a PPG signal captured over a plurality of PPG time windows via a PPG sensor of a wearable device worn by a subject, wherein the received PPG signal is a time series signal; preprocessing the time series signal captured over the plurality of PPG time windows; performing a Singular Spectrum Analysis (SSA) on the pre-processed time series signal of each PPG time window ($PPG_w$) among the plurality of time windows, wherein each PPG time window ($PPG_w$) comprises 'N' signal samples of the preprocessed time series signal. The SSA comprises: a) performing embedding on the pre-processed time series signal corresponding to each PPG time window ($PPG_w$), the embedding comprising: mapping the 'N' signal samples of each PPG time window ($PPG_w$) as a sequence of lagged vectors, wherein length (L) of each lagged vector is equal to width of each PPG time window ($PPG_w$); and creating a trajectory matrix ($P \in \mathbb{R}^{L \times K}$) from the sequence of lagged vectors, wherein number of rows (K) of the trajectory matrix is derived from the length (L) and the 'N' signal samples; b) performing Principal Component Analysis (PCA) on a covariance matrix ($COV_p$) calculated from the trajectory matrix (P) corresponding to each PPG time window ($PPG_w$) to represent elements in the trajectory matrix (P) as a linear combination of basis vectors of the elements, wherein the PCA comprising: deriving a projection matrix ($C \in \mathbb{R}^{L \times K}$) from i) the trajectory matrix (P) and ii) an eigen basis matrix (E), wherein each column of the projection matrix (C) is identified as a principal component ($C_i$) of the received time series signal corresponding to each PPG time window ($PPG_w$), and wherein principal components of the projection matrix (C) corresponding to leading eigen values of the projection matrix (C) associated with each PPG time window ($PPG_w$) are identified as significant principal components and represent a rest tremor signal present the received time series signal; c) reconstructing the rest tremor signal from the significant principal components of the projection matrix (C) of each PPG time window ($PPG_w$) by: reconstructing an inverted matrix ($S \in \mathbb{R}^{L \times K}$) by inverting the projected matrix (C) based on the significant principal components; and performing an antidiagonal averaging on elements of the inverted matrix (S) to obtain rest tremor signal samples corresponding to a reconstructed PPG time window ($PPG_{RW}$) for each PPG time window ($PPG_w$). The method further comprises determining a dominant signal frequency present in the rest tremor signal samples of each reconstructed PPG time window ($PPG_{RW}$) by applying a frequency domain transform.

In another aspect, a system for tremor assessment using Photoplethysmography (PPG). is provided. The system comprises a memory storing instructions; one or more Input/Output (I/O) interfaces; and one or more hardware processors coupled to the memory via the one or more I/O interfaces, wherein the one or more hardware processors are configured by the instructions to receiving a PPG signal captured over a plurality of PPG time windows via a wearable device worn by a subject, wherein the received PPG signal is a time series signal; preprocessing the time series signal captured over the plurality of PPG time windows; performing a Singular Spectrum Analysis (SSA) on the pre-processed time series signal of each PPG time window ($PPG_w$) among the plurality of time windows, wherein each PPG time window ($PPG_w$) comprises 'N' signal samples of the preprocessed time series signal. The SSA comprises: a) performing embedding on the pre-processed time series signal corresponding to each PPG time window ($PPG_w$), the embedding comprising: mapping the 'N' signal samples of each PPG time window ($PPG_w$) as a sequence of lagged vectors, wherein length (L) of each lagged vector is equal to width of each PPG time window ($PPG_w$); and creating a trajectory matrix ($P \in \mathbb{R}^{L \times K}$) from the sequence of lagged vectors, wherein number of rows (K) of the trajectory matrix is derived from the length (L) and the 'N' signal samples; b) performing Principal Component Analysis (PCA) on a covariance matrix ($COV_p$) calculated from the trajectory matrix (P) corresponding to each PPG time window ($PPG_w$) to represent elements in the trajectory matrix (P) as a linear combination of basis vectors of the elements, wherein the PCA comprising: deriving a projection matrix ($C \in \mathbb{R}^{L \times K}$) from i) the trajectory matrix (P) and ii) an eigen basis matrix (E), wherein each column of the projection matrix (C) is identified as a principal component ($C_i$) of the received time series signal corresponding to each PPG time window ($PPG_w$), and wherein principal components of the projection matrix (C) corresponding to leading eigen values of the projection matrix (C) associated with each PPG time window ($PPG_w$) are identified as significant principal components and represent a rest tremor signal present the received time series signal; c) reconstructing the rest tremor signal from the significant principal components of the projection matrix (C) of each PPG time window ($PPG_w$) by: reconstructing an inverted matrix ($S \in \mathbb{R}^{L \times K}$) by inverting the projected matrix (C) based on the significant principal components; and performing an antidiagonal averaging on elements of the inverted matrix (S) to obtain rest tremor signal samples corresponding to a reconstructed PPG time window ($PPG_{RW}$) for each PPG time window ($PPG_w$). The system is further configured to determine a dominant signal frequency present in the rest tremor signal samples of each reconstructed PPG time window ($PPG_{RW}$) by applying a frequency domain transform.

In yet another aspect, there are provided one or more non-transitory machine readable information storage mediums comprising one or more instructions, which when executed by one or more hardware processors causes a method for tremor assessment using Photoplethysmography (PPG). The method comprises receiving a PPG signal captured over a plurality of PPG time windows via a wearable device worn by a subject, wherein the received PPG signal is a time series signal; preprocessing the time series signal captured over the plurality of PPG time windows; performing a Singular Spectrum Analysis (SSA) on the pre-processed time series signal of each PPG time window ($PPG_w$) among the plurality of time windows, wherein each PPG time window ($PPG_w$) comprises 'N' signal samples of the preprocessed time series signal. The SSA comprises: a) performing embedding on the pre-processed time series signal corresponding to each PPG time window ($PPG_w$), the embedding comprising: mapping the 'N' signal samples of each PPG time window ($PPG_w$) as a sequence of lagged vectors, wherein length (L) of each lagged vector is equal to width of each PPG time window ($PPG_w$); and creating a trajectory matrix ($P \in \mathbb{R}^{L \times K}$) from the sequence of lagged vectors, wherein number of rows (K) of the trajectory matrix is derived from the length (L) and the 'N' signal samples; b) performing Principal Component Analysis (PCA) on a covariance matrix ($COV_p$) calculated from the trajectory matrix (P) corresponding to each PPG time window ($PPG_w$) to represent elements in the trajectory matrix (P) as a linear combination of basis vectors of the elements, wherein the PCA comprising: deriving a projection matrix ($C \in \mathbb{R}^{L \times K}$) from i) the trajectory matrix (P) and ii) an eigen basis matrix (E), wherein each column of the projection matrix (C) is identified as a principal component ($C_i$) of the received time series signal corresponding to each PPG time window ($PPG_w$), and wherein principal components of the projection matrix (C) corresponding to leading eigen values of the projection matrix (C) associated with each PPG time window ($PPG_w$) are identified as significant principal components and represent a rest tremor signal present the received time series signal; c) reconstructing the rest tremor signal from the significant principal components of the projection matrix (C) of each PPG time window ($PPG_w$) by: reconstructing an inverted matrix ($S \in \mathbb{R}^{L \times K}$) by inverting the projected matrix (C) based on the significant principal components; and performing an antidiagonal averaging on elements of the inverted matrix (S) to obtain rest tremor signal samples corresponding to a reconstructed PPG time window ($PPG_{RW}$) for each PPG time window ($PPG_w$). The method further comprises determining a dominant signal frequency present in the rest tremor signal samples of each reconstructed PPG time window ($PPG_{RW}$) by applying a frequency domain transform.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
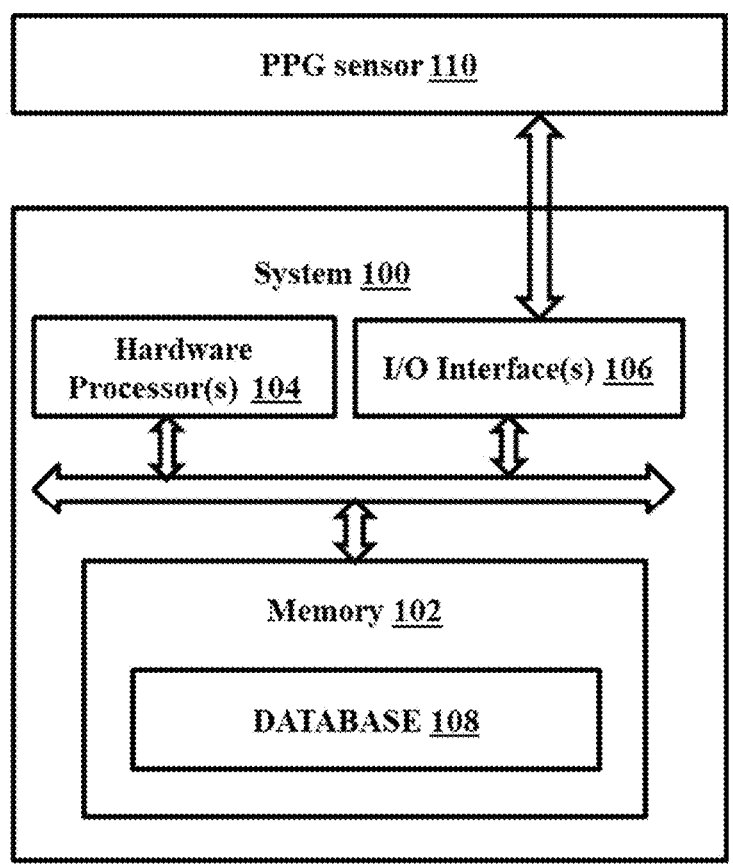
FIG. 1 is a functional block diagram of a system for tremor assessment using Photoplethysmography (PPG), in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Embodiments herein provide a method and system for tremor assessment using Photoplethysmography (PPG). Unlike existing methods, that have limitations in accuracy of the measured tremor signal due to usage of accelerometer sensor with inherent noisy nature, the method and system disclosed herein utilizes a PPG sensor modality for detecting and assessing tremor, alternatively referred as rest tremor. The PPG is an optical method, which measures the changes in blood flow volume at the microvascular bed of tissue of the human body. Conventionally, the PPG sensor is used to detect the Heart Rate or Heart Rate Variability at peripheral sites, such as wrist of a subject to be monitored. Wearable devices such as Smartwatches or Fitness devices are embedded with the PPG sensor due to its unobtrusive approach and a high degree of usability. Thus, PPG sensor is an easily accessible, non-invasive and convenient sensor modality to be used. In the context of Heart Rate estimation, the most challenging issue is the quality of PPG. The PPG sensor is highly sensitive to the motion artifact; thus, the slight movement of hand or vibration of the finger causes a distortion in PPG signal. The method disclosed herein taps this characteristics of the PPG sensor of being sensitive to the motion artifact, as an advantage, to capture tremor signal associated with subject's body part, which is present in the PPG signal of the PPG sensor worn by the subject. Thus, the motion artifact artefact is a true signal for assessment of tremor signal. As can be understood, an acquired PPG signal from the PPG sensor consists of the tremor signal and the cardiac signal along with its harmonics. The method disclosed herein describes an approach to extract tremor signal of interest from the PPG signal by performing a Singular Spectrum Analysis (SSA) followed by spectrum density estimation. The SSA comprises performing embedding on the acquired PPG signal, performing Principal Component Analysis (PCA) on the embedded signal and reconstructing the rest tremor signal from the significant principal components identified post the PCA. Further, the spectrum density estimation detect a dominant frequency present in the principal components, which is the dominant frequency associated with the rest tremor.

Thus, the method enables continuous tremor assessment by deploying wearable device equipped with the PPG sensor in a home environment, wore by the subject, which enables the effective management of treatment.

Figure 2A:
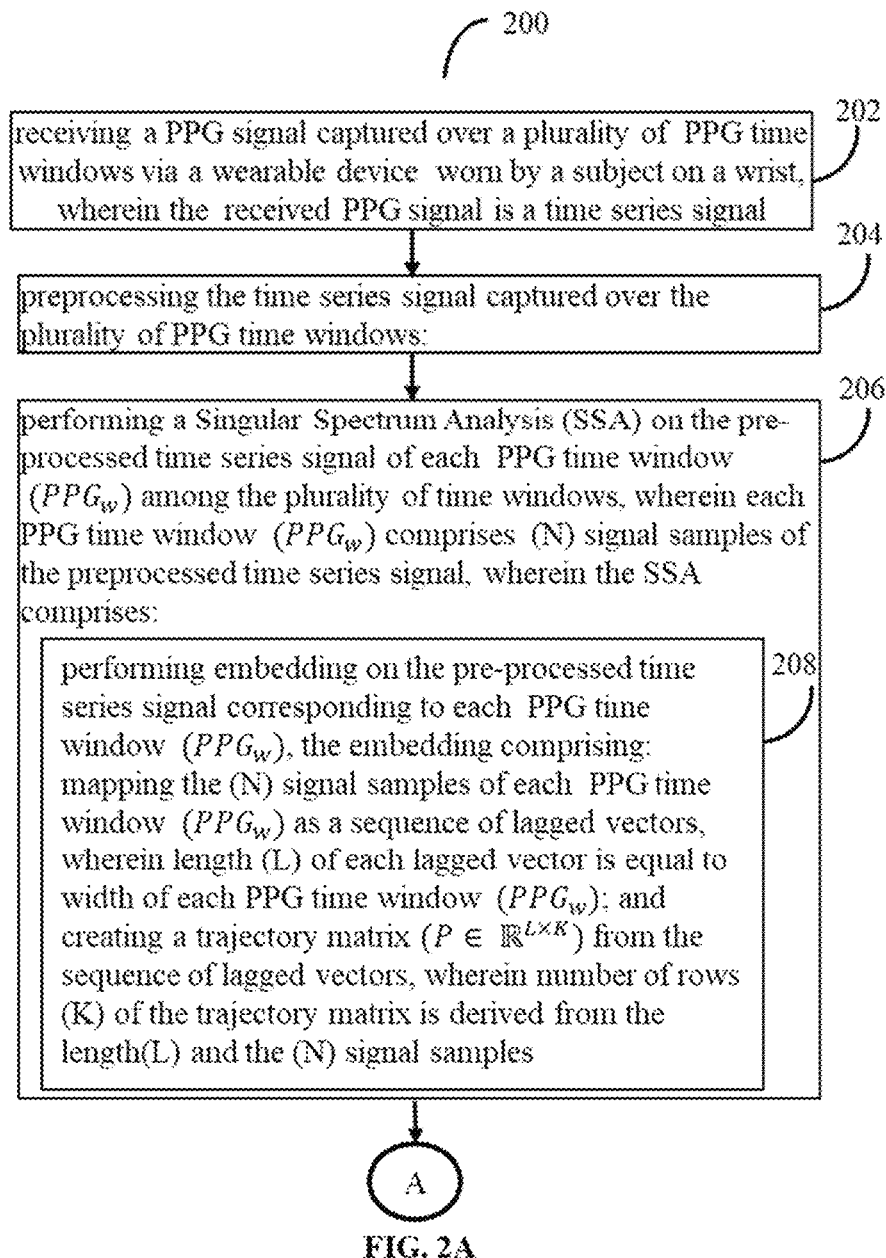
FIGS. 2A through 2C depict a flow diagram illustrating a method for tremor assessment using PPG, implemented by the system of FIG. 1, in accordance with some embodiments of the present disclosure.
Figure 2B:
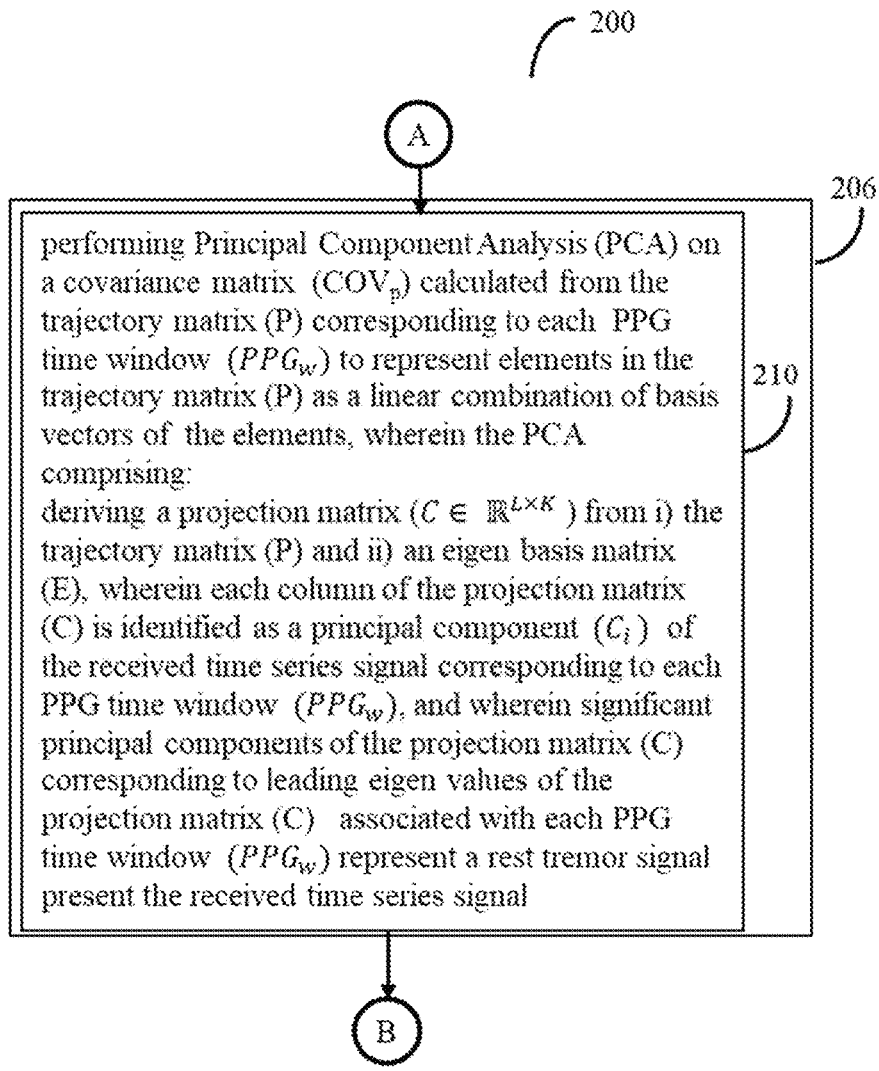
Figure 2C:
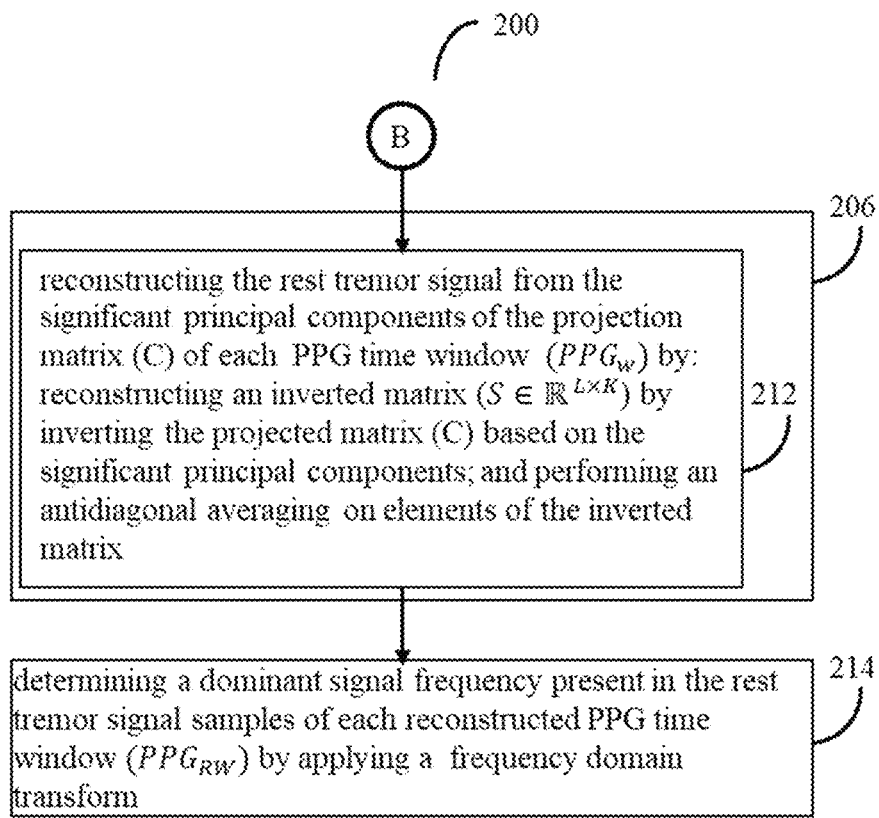
Figure 3:
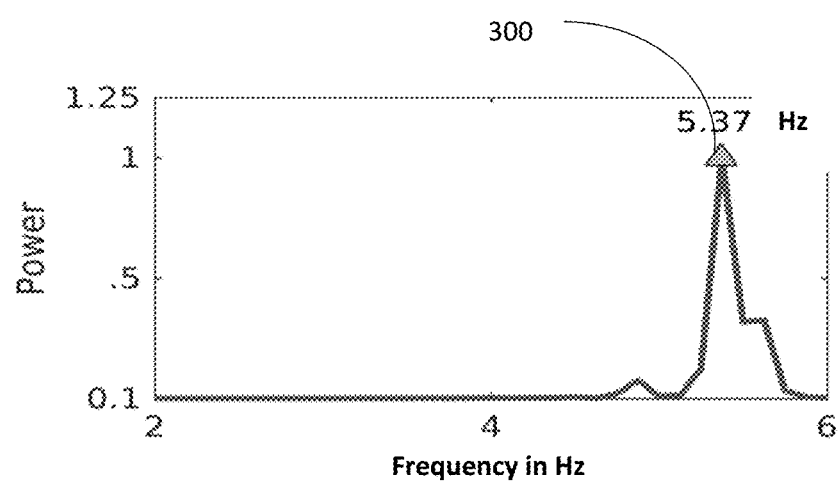
FIG. 3 is a graph illustrating a peak detected in the frequency spectrum of a PPG signal obtained from a wearable device of a particular PPG window, in accordance with some embodiments of the present disclosure.

Referring now to the drawings, and more particularly to FIGS. 1 through 3, where similar reference characters denote corresponding features consistently throughout the figures, there are shown preferred embodiments and these embodiments are described in the context of the following exemplary system and/or method.

FIG. 1 is a functional block diagram of a system 100 for tremor assessment using Photoplethysmography (PPG), in accordance with some embodiments of the present disclosure.

In an embodiment, the system 100 includes a processor(s) 104, communication interface device(s), alternatively referred as input/output (I/O) interface(s) 106, and one or more data storage devices or a memory 102 operatively coupled to the processor(s) 104. The system 100 with one or more hardware processors is configured to execute functions of one or more functional blocks of the system 100.

Referring to the components of system 100, in an embodiment, the processor(s) 104, can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 are configured to fetch and execute computer-readable instructions stored in the memory 102. In an embodiment, the system 100 can be implemented in a variety of computing systems including laptop computers, notebooks, hand-held devices such as mobile phones, workstations, mainframe computers, servers, a network cloud and the like.

The I/O interface(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface (s) 106 can include one or more ports for connecting a number of devices (nodes) of the system 100 to one another or to another server. The I/O interface 106 acquires the PPG signal from a PPG sensor 110 of the system 100. For example, the PPG sensor 110 can be a sensor in a smart watch (wearable device); and processing of the PPG signal for tremor assessment can be performed by the smart watch (system 100). In another embodiment, the PPG sensor 110 may be a sensor within a smart watch or a fitness device attached to the subject's body, while the SSA analysis on the acquired PPG signal for tremor assessment may be carried out by a master device (system 100) connected to the smart watch or the fitness device. Further, for high end analytics by experts, the complete processed data related the tremor assessment is communicated to a server. It is to be understood that the wrist is one preferred position and not a limitation. According to the literature study, the Parkinson's tremor most affects the finger and hand and hence placing fitness devices with PPG sensors on the wrist provides the most appropriate position. Further the smart watch on the wrist is a most realistic and ergonomically attractive option.

However, the PPG sensor can be placed at any position of the body to capture tremor signals associated with corresponding part of the body of the subject.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. Thus, the memory 102 may comprise information pertaining to input(s)/output(s) of each step performed by the processor(s) 104 of the system 100 and methods of the present disclosure.

Further, the memory 102 may include a database 108, which may store the acquired PPG signal captured over multiple PPG time windows. The memory 102 may also include modules (not shown), which are associated with techniques to perform embedding, PCA, rest tremor signal reconstruction and spectrum density estimation. In an embodiment, the database 108 may be external (not shown) to the system 100 and coupled to the system via the I/O interface 106. Functions of the components of system 100 are explained in conjunction with flow diagram of FIGS. 2A and 2B for tremor assessment using PPG.

FIGS. 2A through 2C depict a flow diagram of a method for data tremor assessment using the PPG, implemented by the system of FIG. 1, in accordance with some embodiments of the present disclosure.

In an embodiment, the system 100 comprises one or more data storage devices or the memory 102 operatively coupled to the processor(s) 104 and is configured to store instructions for execution of steps of the method 200 by the processor(s) or one or more hardware processors 104. The steps of the method 200 of the present disclosure will now be explained with reference to the components or blocks of the system 100 as depicted in FIG. 1 and the steps of flow diagram as depicted in FIGS. 2A through 2C. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

The method 200 disclosed herein provides tremor signal extraction from the acquired PPG signal using a Non-Parametric approach. Inherently, the PPG signal consist of a slowly varying signal associated with cardiac rhythm. Considering the Heart Rate ranges 45 beats per minute (BPM) to 180 BPM, the desired PPG signal's range is 0.75 Hertz (Hz) to 3 Hz. Notably, the range of Parkinson's Tremor lies in 4 to 6 Hz. Thus, the conventional filtering method applied on the acquired PPG signal should be adequate to extract the tremor signal. However, this theory works appropriately until the harmonics of the heart rate signal gets overlapped with the tremor signal. In order to overcome this, instead of conventional filtering, the method disclosed provides a signal decomposition technique to identify the rest tremor. The signal decomposition approach disclosed herein converts the PPG signal, which is a time series signal, into number of constitutive components and eventually extracts the signal of interest (rest tremor) according to a criterion explained in conjunction with the PCA steps described later. The Singular Spectrum Analysis (SSA) is employed as a signal decomposing technique, which essentially utilizes the Principal Component Analysis for signal decomposition.

Referring to the steps of the method 200, at step 202, one or more hardware processors 104 are configured to receive a PPG signal captured over a plurality of PPG time windows via the PPG sensor 110 of a wearable device worn by a subject, wherein the received PPG signal is a time series signal.

At step 204 of the method 200, the one or more hardware processors 104 are configured to preprocess the time series signal captured over the plurality of PPG time windows. The pre-processing conditions the acquired PPG signal and filters noise to provide a clean signal for SSA analysis.

At step 206 of the method 200, the one or more hardware processors 104 are configured to perform the Singular Spectrum Analysis (SSA) on the pre-processed time series signal of each PPG time window ($PPG_w$) among the plurality of time windows. Each PPG time window ($PPG_w$) comprises 'N' signal samples of the preprocessed time series signal.

The SSA approach used by the method 200 is explained in conjunction with steps 208 through 212. At step 208, one or more hardware processors 104 are configured to a) performing embedding on the pre-processed time series signal corresponding to each PPG time window ($PPG_w$), the embedding comprising: mapping the 'N' signal samples of each PPG time window ($PPG_w$) as a sequence of lagged vectors, wherein length (L) of each lagged vector is equal to width of each PPG time window ($PPG_w$); and creating a trajectory matrix ($P \in \mathbb{R}^{L \times K}$) from the sequence of lagged vectors, wherein number of rows (K) of the trajectory matrix is derived from the length (L) and the 'N' signal samples. Given the PPG signal ($PPG_w = p_1, p_2 \ldots p_N$), where N is the number of samples in a particular time window. The signal is converted into L lagged vectors. The L is denoted as the window length. It can be noted that, for a meaningful projection, L is chosen as $$L < \frac{N}{2}$$

The trajectory matrix (P) of the PPG window ($PPG_w$) is devised where, the number of rows (K) of the trajectory matrix is equal to (N−L+1).

$$PPG_w => p_{i,j} = \begin{bmatrix} p_1 & p_2 & \cdots & p_L \\ p_2 & \cdots & p_3 & \cdots & \vdots \\ p_k & p_{k+1} & \cdots & \cdots & p_N \end{bmatrix}$$

The trajectory matrix P manifests two salient properties: 1) rows and columns are the subseries of the PPG signal window and 2) Cross-diagonals of (P) is $p_{j+1-i} = p_{i+j-1}$.

Once the trajectory matrix (P) is obtained, at step 210, one or more hardware processors 104 are configured to perform the Principal Component Analysis (PCA) on a covariance matrix ($COV_p$) calculated from the trajectory matrix (P) corresponding to each PPG time window ($PPG_w$) to represent elements in the trajectory matrix (P) as a linear combination of basis vectors of the elements. The PCA comprising deriving a projection matrix ($C \in \mathbb{R}^{L \times K}$) from i) the trajectory matrix (P) and ii) an eigen basis matrix (E). Each column of the projection matrix (C) is identified as a principal component ($C_1$) of the received time series signal corresponding to each PPG time window ($PPG_w$) and wherein principal components of the projection matrix (C) corresponding to leading eigen values of the projection matrix (C) associated with each PPG time window (PPG$_w$) are identified as significant principal components and represent a rest tremor signal present in the received time series signal.

For the projected matrix:

$$C = PE \quad (1)$$

where (E∈ $\mathbb{R}^{L \times K}$) and represents the eigenbasis matrix (of eigen vectors) computed from the covariance matrix (COV$_p$) of the trajectory matrix (P) and a transpose matrix (P$^T$), and wherein $$COV_p = \frac{1}{N-1} PP^T \quad (2)$$

where, N is the number of samples in a particular time window and represents the dimension.

The eigenbasis exploits the temporal covariance of the PPG signal, represented as lagged vectors in trajectory matrix (P). Every column of the projected matrix (C∈ $\mathbb{R}^{L \times K}$) are denoted as principal components. These principal components are the subseries and associates with the major components of the original signal. Essentially, in generalized form, the original PPG signal is decomposed and approximated into a number of constitutive components is:

$$PPG_w \approx \Sigma_{i=1}^N C(i) \quad (3)$$

At step 212, one or more hardware processors 104 are configured to reconstructing the rest tremor signal from the significant principal components of the projection matrix (C) of each PPG time window (PPG$_w$) by: reconstructing an inverted matrix (S∈ $\mathbb{R}^{L \times K}$) by inverting the projected matrix (C) based on the significant principal components; and performing an antidiagonal averaging on elements of the inverted matrix (S) to obtain rest tremor signal samples corresponding to a reconstructed PPG time window (PPG$_{RW}$) for each PPG time window (PPG$_w$). Herein, the hypothesized that the major principal component denoted by the leading eigenvalue, represents the tremor component of the signal. After eigen decomposition, eigen vectors are generated along with corresponding eigen values. Based on the eigen values, the eigen vectors are organized in order and eigen values above a predefined value are considered as the leading eigen values. It is imperative to note that, the rest tremor is the major component in PPG signal and poses a higher variance compares to the harmonics of heart signal or any other sensor noises. Since PCA learns the projection matrix by emphasizing the variance of the signal; implicitly, it could be stated the leading Principal component is associated with rest tremor. In order to reconstruct the time series, the projection of the trajectory matrix (P) on eigenbasis is inverted. This inversion operation is accomplished only using the leading principal component. Considering the leading principal component (C∈ $\mathbb{R}^{L \times K}$) and corresponding eigen vector (E∈ $\mathbb{R}^{L \times K}$); the inverted projection is defined as:

$$S = CE \quad (4)$$

Where, S is the reconstructed components. This leads to the reconstructed matrix S∈ $\mathbb{R}^{L \times K}$, which contains the time series signal contributed by leading principal component. The anti-diagonal averaging is performed to reconstruct the elements in the time series window. If (PPG$_{RW}$(n), n=1, 2, ... N) is considered as the reconstructed time window, then the diagonal averaging process is defined by the following equation.

$$PPG_{RW}(n) = \begin{cases} \frac{1}{n}\sum_{m=1}^{n} S(m, n-m+1) \forall\ 1 \le n \le L \\ \frac{1}{L}\sum_{m=1}^{L} S(m, n-m+1) \forall\ L \le n \le K \\ \frac{1}{N-n+1}\sum_{m=N-n+1}^{L} S(m, n-m+1) \forall\ (K+1) \le n \le N \end{cases} \quad (5)$$

Upon reconstruction of the rest tremor or rest tremor signal, at step 214 of the method 200, the one or more hardware processors 104 are configured to determine a dominant signal frequency present in the rest tremor signal samples of each reconstructed PPG time window (PPG$_{RW}$) by applying a frequency domain transform. Since the tremor signal is essentially an oscillation signal, leveraged is the spectrum density estimation for tremor estimation. The Fast Fourier Transform (FFT) is applied on the reconstructed signal acquired after SSA to obtain the dominant frequency. The dominant frequency associated with rest tremor is used as a reference parameter for further processing. FIG. 3 shows the peak 300 detected in the frequency spectrum of the PPG signal obtained from the smartwatch of a particular window of data. This PPG signal is processed using SSA before applying the FFT.

The dominant frequency is denoted as tremor frequency, indicating that the hand or finger is vibrating with this frequency. This is important information along with the amplitude for neurologist (expert) who can prescribe the medicine according to the intensity and frequency of tremor. The experts can refer to the to the severity of the symptom, the dose of the medications needs to be altered. Presently, the quantitative assessment of the symptom is ascertained by the various rating scales standards such as Unified Parkinson's Disease Rating Scale (UPDRS) or Hoehn and Yahr scale. The UPDRS scale is the most widely used assessment procedure, accomplished in the clinical environment by expert neurologists. The UPDRS has four subscales. The motor dysfunctions are designated in Subscale 3. The Subscale 3 constitutes 14 types of rating, Rest Tremor is one of them. The Rest Tremor rating is categorized by the following scoring:

TABLE 1

| Rating | Description |
| --- | --- |
| 0 | None |
| 1 | slight or infrequently present |
| 2 | moderate in amplitude and intermittent |
| 3 | moderate in amplitude and persistent |
| 4 | marked in amplitude and persistent |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for tremor assessment using Photoplethysmography (PPG), comprising:
   receiving, by one or more hardware processors, a PPG signal captured over a plurality of PPG time windows via a PPG sensor of a wearable device worn by a subject, wherein the received PPG signal is a time series signal;
   preprocessing, by the one or more hardware processors, the time series signal captured over the plurality of PPG time windows;
   filtering a noise from the preprocessed time series signal;
   performing, by the one or more hardware processors, a Singular Spectrum Analysis (SSA) on the pre-processed time series signal of each PPG time window ($PPG_w$) among the plurality of time windows, wherein each PPG time window ($PPG_w$) comprises 'N' signal samples of the preprocessed time series signal, wherein the SSA comprises is performed by:
   a) performing embedding on the pre-processed time series signal corresponding to each PPG time window ($PPG_w$), wherein the embedding comprises:
      mapping the 'N' signal samples of each PPG time window ($PPG_w$) as a sequence of lagged vectors, wherein a length (L) of each lagged vector of the sequence of lagged vectors is equal to a width of each PPG time window ($PPG_w$); and
      creating a trajectory matrix ($P \in \mathbb{R}^{L \times K}$) from the sequence of lagged vectors, wherein a number of rows (K) of the created trajectory matrix is derived from the length (L) of each lagged vector and the 'N' signal samples;
   b) performing Principal Component Analysis (PCA) on a covariance matrix ($COV_p$), wherein the covariance matrix ($COV_p$) is calculated from the trajectory matrix (P) corresponding to each PPG time window ($PPG_w$) to represent elements in the trajectory matrix (P) as a linear combination of basis vectors of the elements, wherein the PCA comprises:
      deriving a projection matrix ($C \in \mathbb{R}^{L \times K}$) from each of:
      i) the trajectory matrix (P), and
      ii) an eigen basis matrix (E), wherein
         each column of the projection matrix (C) is identified as a principal component ($C_i$) of the time series signal corresponding to each PPG time window ($PPG_w$),
         principal components of the projection matrix (C) corresponding to leading eigen values of the projection matrix (C) associated with each PPG time window ($PPG_w$) are identified as significant principal components, and
         the significant principal components represent a rest tremor signal present in the time series signal; and
   c) reconstructing the rest tremor signal from the significant principal components of the projection matrix (C) of each PPG time window ($PPG_w$) by:
      reconstructing an inverted matrix ($S \in \mathbb{R}^{L \times K}$) by inverting the projected matrix (C) using the significant principal components; and
      performing an antidiagonal averaging on elements of the inverted matrix (S) to obtain rest tremor signal samples corresponding to a reconstructed PPG time window ($PPG_{RW}$) for each PPG time window ($PPG_w$);

determining, by the one or more hardware processors, a dominant signal frequency present in the rest tremor signal samples of each reconstructed PPG time window ($PPG_{RW}$) by applying a frequency domain transform on the reconstructed rest tremor signal, wherein
the dominant signal frequency is denoted as a tremor frequency, and
the tremor frequency indicates that a hand of the subject or a finger of the subject is vibrating with the dominant signal frequency; and providing, based on the tremor frequency and a rating scale of the rest tremor signal, a dose of medications to the subject, wherein
the rating scale of the rest tremor signal includes a rating 0, a rating 1, a rating 2, a rating 3, and a rating 4,
the rating 0 indicates no conditions of a Parkinson's Disease,
the rating 1 indicates one of a slight or infrequently condition of the Parkinson's Disease,
the rating 2 indicates a moderate in amplitude and an intermittent condition of the Parkinson's Disease,
the rating 3 indicates the moderate in amplitude and a persistent condition of the Parkinson's Disease, and
the rating 4 indicates the marked in amplitude and the persistent condition of the Parkinson's Disease.

2. The processor implemented method of claim 1, wherein the length (L) is less than half of the 'N' signal samples.

3. The processor implemented method of claim 1, wherein the number of rows (K) of the trajectory matrix is equal to (N−L+1).

4. The processor implemented method of claim 1, wherein the projection matrix (C) is a product of the trajectory matrix (P) and the eigen basis matrix (E).

5. The processor implemented method of claim 1, wherein the eigen basis matrix (E) is obtained from a covariance matrix ($COV_p$) of the trajectory matrix (P) and a transpose matrix ($P^T$), and wherein $$COV_p = \frac{1}{N-1} PP^T.$$

6. The processor implemented method of claim 1, wherein the frequency domain transform is a Fast Fourier Transform (FFT).

7. A system for tremor assessment using Photoplethysmography (PPG), comprising:
a memory storing instructions;
one or more Input/Output (I/O) interfaces; and
one or more hardware processors coupled to the memory via the one or more I/O interfaces, wherein the one or more hardware processors are configured by the instructions to perform the following steps:
receive a PPG signal captured over a plurality of PPG time windows via a PPG sensor of a wearable device worn by a subject, wherein the received PPG signal is a time series signal;
preprocess, the time series signal captured over the plurality of PPG time windows;
filter a noise from the preprocessed time series signal;
perform a Singular Spectrum Analysis (SSA) on the filtered pre-processed time series signal of each PPG time window ($PPG_w$) among the plurality of time windows, wherein each PPG time window ($PPG_w$) comprises 'N' signal samples of the preprocessed time series signal, wherein the SSA comprises:
a) performing embedding on the pre-processed time series signal corresponding to each PPG time window ($PPG_w$), wherein the embedding comprises:
mapping the 'N' signal samples of each PPG time window ($PPG_w$) as a sequence of lagged vectors, wherein length (L) of each lagged vector of the sequence of lagged vectors is equal to a width of each PPG time window ($PPG_w$); and
creating a trajectory matrix ($P \in \mathbb{R}^{L \times K}$) from the sequence of lagged vectors, wherein a number of rows (K) of the created trajectory matrix is derived from the length (L) and the 'N' signal samples;
b) performing Principal Component Analysis (PCA) on a covariance matrix ($COV_p$), wherein the covariance matrix ($COV_p$) is calculated from the trajectory matrix (P) corresponding to each PPG time window ($PPG_w$) to represent elements in the trajectory matrix (P) as a linear combination of basis vectors of the elements, wherein the PCA comprises:
deriving a projection matrix ($C \in \mathbb{R}^{L \times K}$) from each of:
i) the trajectory matrix (P), and
ii) an eigen basis matrix (E), wherein
each column of the projection matrix (C) is identified as a principal component ($C_i$) of the time series signal corresponding to each PPG time window ($PPG_w$), and
principal components of the projection matrix (C) corresponding to leading eigen values of the projection matrix (C) associated with each PPG time window ($PPG_w$) are identified as significant principal components, and
the significant principal components represent a rest tremor signal present in the received time series signal; and
c) reconstructing the rest tremor signal from the significant principal components of the projection matrix (C) of each PPG time window ($PPG_w$) by:
reconstructing an inverted matrix ($S \in \mathbb{R}^{L \times K}$) by inverting the projected matrix (C) using the significant principal components; and
performing an antidiagonal averaging on elements of the inverted matrix (S) to obtain rest tremor signal samples corresponding to a reconstructed PPG time window ($PPG_{RW}$) for each PPG time window ($PPG_w$);
determine a dominant signal frequency present in the rest tremor signal samples of each reconstructed PPG time window ($PPG_{RW}$) by applying a frequency domain transform on the reconstructed rest tremor signal, wherein
the dominant signal frequency is denoted as a tremor frequency, and
the tremor frequency indicates that a hand of the subject or a finger of the subject is vibrating with the dominant signal frequency; and
provide, based on the tremor frequency and a rating scale of the tremor frequency, a dose of medications to the subject, wherein the rating scale of the tremor frequency includes a rating 0, a rating 1, a rating 2, a rating 3, and a rating 4, the rating 0 indicates no conditions of a Parkinson's Disease, the rating 1 indicates one of a slight or infrequently condition of the Parkinson's Disease, the rating 2 indicates a moderate in amplitude and an intermittent condition of the Parkinson's Disease, the rating 3 indicates the moderate in amplitude and a persistent condition of the Parkinson's Disease, and the rating 4 indicates the marked in amplitude and the persistent condition of the Parkinson's Disease.

8. The system of claim 7, wherein the length (L) is less than half of the 'N' signal samples.

9. The system of claim 7, wherein the number of rows (K) of the trajectory matrix is equal to (N−L+1).

10. The system of claim 7, wherein the projection matrix (C) is a product of the trajectory matrix (P) and the eigen basis matrix (E).

11. The system of claim 7, wherein the eigen basis matrix (E) is obtained from a covariance matrix ($COV_p$) of the trajectory matrix (P) and a transpose matrix ($P^T$), and wherein $$COV_p = \frac{1}{N-1} PP^T.$$

12. The system of claim 7, wherein the frequency domain transform is a Fast Fourier Transform (FFT).

13. One or more non-transitory machine readable information storage mediums comprising one or more instructions, which when executed by one or more hardware processors causes:

receiving a PPG signal captured over a plurality of PPG time windows via a PPG sensor of a wearable device worn by a subject, wherein the received PPG signal is a time series signal;

preprocessing the time series signal captured over the plurality of PPG time windows;

filtering, a noise from the pre-processed time series signal;

performing a Singular Spectrum Analysis (SSA) on the filtered pre-processed time series signal of each PPG time window ($PPG_w$) among the plurality of time windows, wherein each PPG time window ($PPG_w$) comprises 'N' signal samples of the preprocessed time series signal, wherein the SSA comprises:

a) performing embedding on the pre-processed time series signal corresponding to each PPG time window ($PPG_w$), wherein the embedding comprises:

mapping the 'N' signal samples of each PPG time window ($PPG_w$) as a sequence of lagged vectors, wherein a length (L) of each lagged vector of the sequence of lagged vectors is equal to a width of each PPG time window ($PPG_w$); and creating a trajectory matrix ($P \in \mathbb{R}^{L \times K}$) from the sequence of lagged vectors, wherein a number of rows (K) of the trajectory matrix is derived from the length (L) of each lagged vector and the 'N' signal samples;

b) performing Principal Component Analysis (PCA) on a covariance matrix ($COV_p$), wherein the covariance matrix ($COV_p$) is calculated from the trajectory matrix (P) corresponding to each PPG time window ($PPG_w$) to represent elements in the trajectory matrix (P) as a linear combination of basis vectors of the elements, wherein the PCA comprises:

deriving a projection matrix ($C \in \mathbb{R}^{L \times K}$) from each of:

i) the trajectory matrix (P) and ii) an eigen basis matrix (E), wherein each column of the projection matrix (C) is identified as a principal component ($C_i$) of the time series signal corresponding to each PPG time window ($PPG_w$), principal components of the projection matrix (C) corresponding to leading eigen values of the projection matrix (C) associated with each PPG time window ($PPG_w$) are identified as significant principal components, and the significant principal components represent a rest tremor signal present in the received time series signal; and c) reconstructing the rest tremor signal from the significant principal components of the projection matrix (C) of each PPG time window ($PPG_w$) by:

reconstructing an inverted matrix ($S \in \mathbb{R}^{L \times K}$) by inverting the projected matrix (C) using the significant principal components; and performing an antidiagonal averaging on elements of the inverted matrix (S) to obtain rest tremor signal samples corresponding to a reconstructed PPG time window ($PPG_{RW}$) for each PPG time window ($PPG_w$);

determining a dominant signal frequency present in the rest tremor signal samples of each reconstructed PPG time window ($PPG_{RW}$) by applying a frequency domain transform on the reconstructed rest tremor signal, wherein the dominant signal frequency is denoted as a tremor frequency, and the tremor frequency indicates that a hand of the subject or a finger of the subject is vibrating with the dominant signal frequency; and providing, based on the tremor frequency, and a rating scale of the rest tremor signal, a dose of medications to the subject, wherein the rating scale of the rest tremor signal includes a rating 0, a rating 1, a rating 2, a rating 3, and a rating 4, the rating 0 indicates no conditions of the Parkinson's Disease, the rating 1 indicates one of a slight or infrequently condition of the Parkinson's Disease, the rating 2 indicates a moderate in amplitude and an intermittent condition of the Parkinson's Disease, the rating 3 indicates the moderate in amplitude and a persistent condition of the Parkinson's Disease, and the rating 4 indicates the marked in amplitude and the persistent condition of the Parkinson's Disease.

* * * * *